(12) United States Patent
Sun et al.

(10) Patent No.: US 8,637,067 B1
(45) Date of Patent: Jan. 28, 2014

(54) ELASTIC TISSUE MATRIX DERIVED HYDROGEL

(75) Inventors: Wenquan Sun, Warrington, PA (US); Hui Xu, Plainsboro, NJ (US); Hua Wan, Princeton, NJ (US)

(73) Assignee: LifeCell Corporation, Branchburg, NH (US)

( * ) Notice: Subject to any disclaimer, the term of this patent is extended or adjusted under 35 U.S.C. 154(b) by 0 days.

(21) Appl. No.: 13/415,355

(22) Filed: Mar. 8, 2012

Related U.S. Application Data

(60) Provisional application No. 61/451,315, filed on Mar. 10, 2011.

(51) Int. Cl.
*A61F 2/00* (2006.01)
*A61F 2/02* (2006.01)

(52) U.S. Cl.
USPC ........................................ 424/426; 623/23.72

(58) Field of Classification Search
None
See application file for complete search history.

(56) References Cited

U.S. PATENT DOCUMENTS

| | | | |
|---|---|---|---|
| 5,336,616 A | 8/1994 | Livesey et al. | |
| 5,364,756 A | 11/1994 | Livesey et al. | |
| 6,166,288 A | 12/2000 | Diamond et al. | |
| 6,381,026 B1 | 4/2002 | Schiff et al. | |
| 6,933,326 B1 | 8/2005 | Griffey et al. | |
| 7,358,284 B2 | 4/2008 | Griffey et al. | |
| 7,425,322 B2 | 9/2008 | Cohn et al. | |
| 7,799,767 B2 * | 9/2010 | Lamberti et al. | 514/80 |
| 7,815,561 B2 * | 10/2010 | Forman et al. | 600/3 |
| 7,838,021 B2 | 11/2010 | Lafont et al. | |
| 2003/0035843 A1 | 2/2003 | Livesey et al. | |
| 2003/0143207 A1 | 7/2003 | Livesey et al. | |
| 2005/0008672 A1 | 1/2005 | Winterbottom et al. | |
| 2005/0028228 A1 * | 2/2005 | McQuillan et al. | 800/17 |
| 2005/0118230 A1 * | 6/2005 | Hill et al. | 424/426 |
| 2006/0073592 A1 * | 4/2006 | Sun et al. | 435/423 |
| 2006/0115515 A1 | 6/2006 | Pirhonen et al. | |
| 2006/0210960 A1 | 9/2006 | Livesey et al. | |
| 2007/0009586 A1 | 1/2007 | Cohen et al. | |
| 2007/0104759 A1 | 5/2007 | Dunn et al. | |
| 2007/0248575 A1 | 10/2007 | Connor et al. | |
| 2008/0027562 A1 | 1/2008 | Fujisato et al. | |
| 2009/0130221 A1 | 5/2009 | Bolland et al. | |
| 2009/0306790 A1 * | 12/2009 | Sun | 623/23.72 |
| 2010/0021961 A1 | 1/2010 | Fujisato et al. | |
| 2011/0020271 A1 * | 1/2011 | Niklason et al. | 424/85.2 |
| 2012/0040013 A1 | 2/2012 | Owens et al. | |

FOREIGN PATENT DOCUMENTS

| WO | WO 03/017826 A2 | 3/2003 |
|---|---|---|
| WO | WO 2007/043513 A1 | 4/2007 |
| WO | WO 2007/134134 A2 | 11/2007 |

OTHER PUBLICATIONS

Collins et al., "Cardiac xenografts between primate species provide evidence for the importance of the α-galactosyl determinant in hyperacute rejection" *J. Immunol.*, 154:5500-5510 (1995).
Dobrin et al., "Elastase, collagenase, and the biaxial elastic properties of dog carotid artery" *Am. J. Physiol. Heart Circ. Physiol.*, 247:H124-H131 (1984).
Galili et al., "Man, Apes, and Old World Monkeys Differ from Other Mammals in the Expression of α-Galactosyl Epitopes on Nucleated Cells" *J. Biol. Chem.*, 263(33):17755-17762 (1988).
Galili et al., "Interaction Between Human Natural Anti-α-Galactosyl Immunoglobulin G and Bacteria of the Human Flora" *Infect. Immun.*, 56(7):1730-1737 (1988).
Galili et al., "Interaction of the Natural Anti-Gal Antibody with α-Galactosyl Epitopes: a Major Obstacle for Xenotransplantation in Humans" *Immunology Today*, 14(10):480-482 (1993).
Good et al., "Identification of carbohydrate structures that bind human antiporcine antibodies: implications for discordant xenografting in humans" *Transplant. Proc.*, 24:559-562 (1992).
Hamadeh et al., "Human natural anti-Gal IgG regulates alternative complement pathway activation on bacterial surfaces" *J. Clin. Invest.*, 89:1223-1235 (1992).
International Search Report and Written Opinion issued in International Patent Application No. PCT/US2009/046193, mailed Jul. 30, 2010.
International Search Report and Written Opinion issued in International Patent Application No. PCT/US2011/047041, mailed Oct. 25, 2011.
Karlinsky et al., "In Vitro Effects of Elastase and Collagenase on Mechanical Properties of Hamster Lungs" *Chest*, 69(2 Suppl.):275-276 (1976).
Lee, et al., "In vitro evaluation of a poly(lactide-*co*-glycolide)-collagen composite scaffold for bone regeneration," *Biomaterials*, 27:3466-3472 (2006).
Lu et al., "Novel Porous Aortic Elastin and Collagen Scaffolds for Tissue Engineering" *Biomaterials*, 25(22):5227-5237 (2004).
Reihsner et al., "Biomechanical properties of elastase treated palmar aponeuroses" *Connective Tissue Research*, 26:77-86 (1991).
Sandor et al., "Host response to implanted porcine-derived biologic materials in a primate model of abdominal wall repair," *Tissue Engineering: Part A*, 14(12):2021-2031 (2008).
Sandrin et al., "Anti-pig IgM antibodies in human serum react predominantly with Gal(alpha 1-3)Gal epitopes" *Proc. Natl. Acad. Sci. USA*, 90:11395-11395 (1993).
Tedder et al., "Stabilized Collagen Scaffolds for Heart Valve Tissue Engineering" *Tissue Engineering: Part A* 00(00):1-12 (2008).
U.S. Appl. No. 12/478,435, filed Jun. 4, 2009 by Sun: Non-Final Office Action, dated Jan. 13, 2012.
U.S. Appl. No. 12/478,435, filed Jun. 4, 2009 by Sun: Final Office Action, dated Apr. 30, 2012.
Xu et al., "A Porcine-Derived Acellular Dermal Scaffold That Supports Soft Tissue Regeneration: Removal of Terminal Galactose-α-(1,3)-Galactose and Retention of Matrix Structure," *Tissue Engineering: Part A*, 15(00):1-13 (2009).
Yuan et al., "Effects of collagenase and elastase on the mechanical properties of lung tissue strips" *J. App. Physiol.* 89:3-14 (2000).

* cited by examiner

*Primary Examiner* — Robert A Wax
*Assistant Examiner* — Danah Al-Awadi
(74) *Attorney, Agent, or Firm* — McCarter & English, LLP; Matthew R. Van Eman

(57) ABSTRACT

A tissue-derived hydrogel, as well as methods of making and using such hydrogels, are provided.

6 Claims, 10 Drawing Sheets

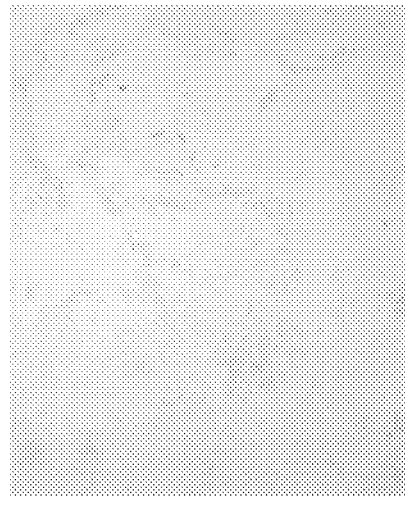
FIG. 4A FRESH AORTA, H&E STAIN
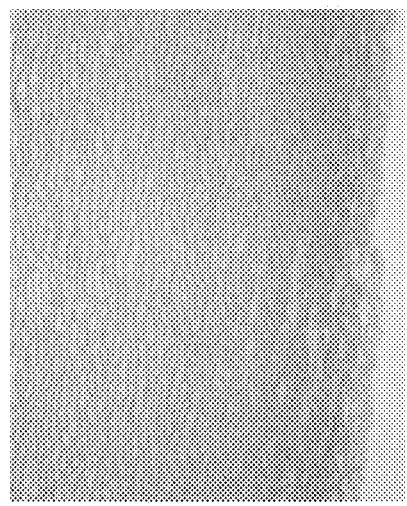
FIG. 4B DECELLULARIZED, H&E STAIN
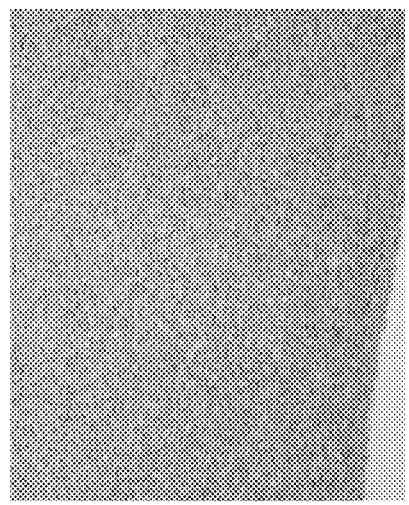
FIG. 4C ELASTASE TREATED, H&E STAIN
FIG. 4D FRESH AORTA, VERHOFF'S STAIN
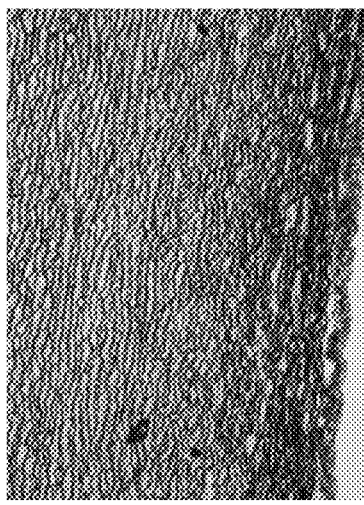
FIG. 4E DECELLULARIZED, VERHOFF'S STAIN
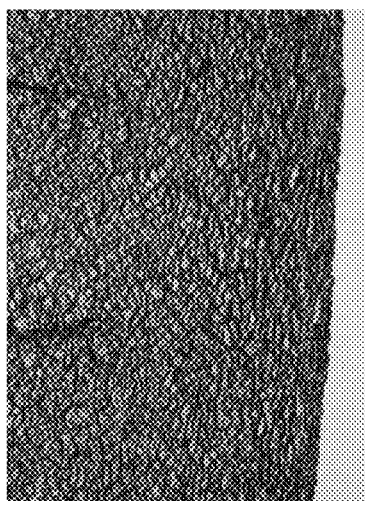
FIG. 4F ELASTASE TREATED, VERHOFF'S STAIN

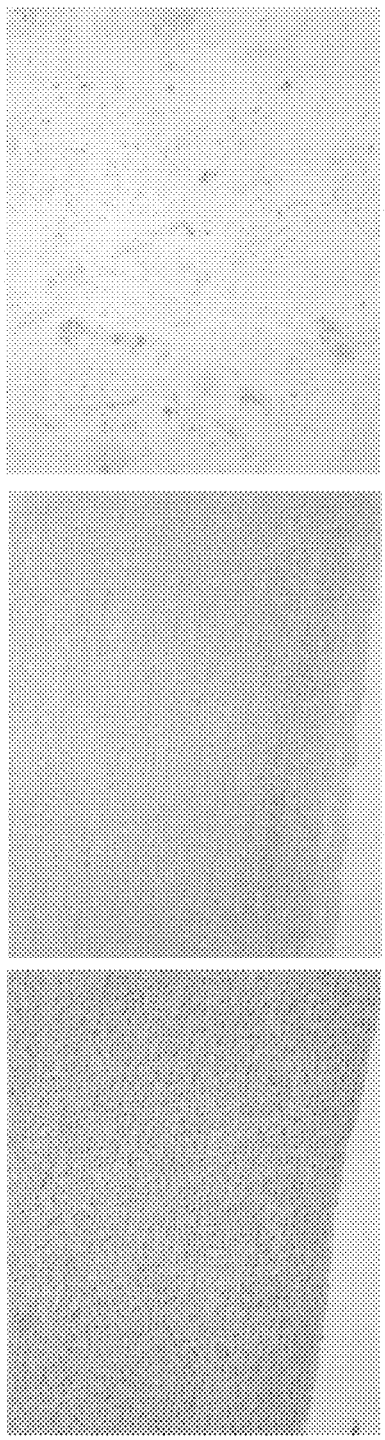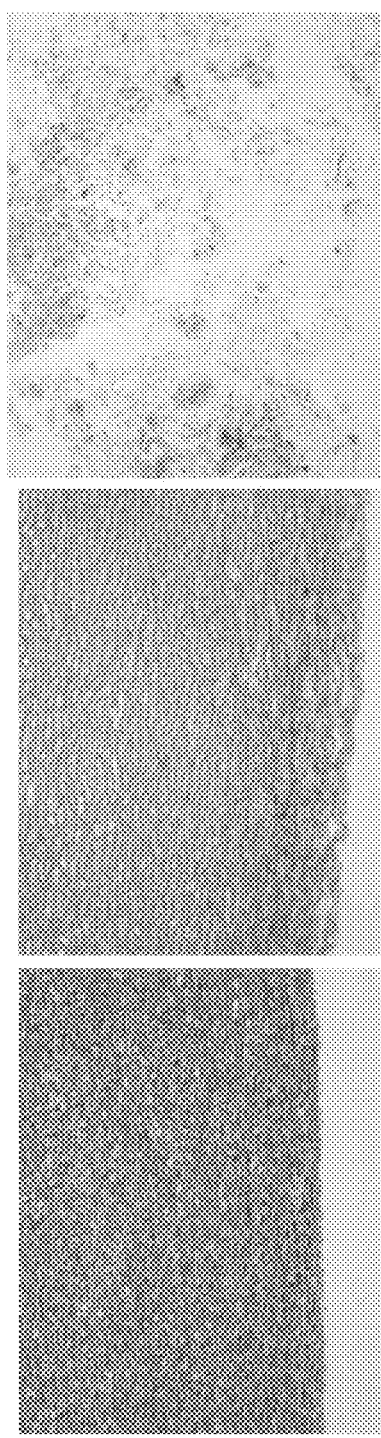

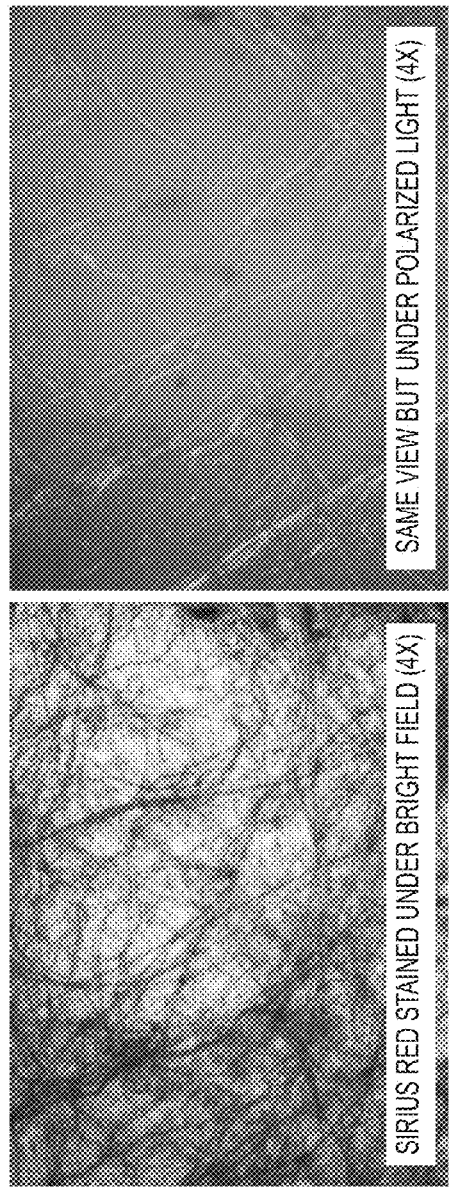
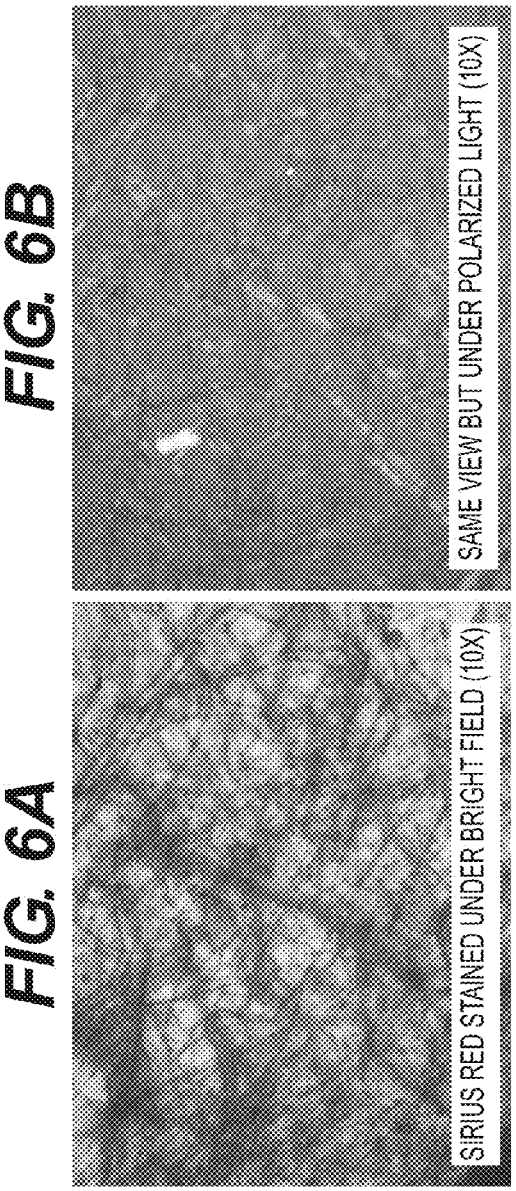
FIG. 6A — SIRIUS RED STAINED UNDER BRIGHT FIELD (4X)
FIG. 6B — SAME VIEW BUT UNDER POLARIZED LIGHT (4X)
FIG. 6C — SIRIUS RED STAINED UNDER BRIGHT FIELD (10X)
FIG. 6D — SAME VIEW BUT UNDER POLARIZED LIGHT (10X)

ELASTIC TISSUE MATRIX DERIVED HYDROGEL

This application claims priority under 35 U.S.C. §119 to U.S. provisional application No. 61/451,315, filed on Mar. 10, 2011, which is incorporated herein by reference in its entirety.

The present disclosure relates generally to tissue-derived hydrogels and methods of making and using hydrogels for various therapeutic purposes.

Hydrogels have a number of medical and surgical applications, including their use as drug carriers for controlled medicinal delivery, as soft tissue fillers, as wound dressings, and as scaffolds for tissue treatment, regeneration, and/or repair. Existing hydrogels are made from various biomaterials of synthetic and biological origin. However, the extensive chemical modification and synthetic materials required to produce existing hydrogels result in poor biocompatibility that can hinder tissue treatment or regeneration.

In certain embodiments, a tissue-derived hydrogel is provided. The hydrogel comprises an acellular arterial tissue matrix that has been treated with an elastase to form a hydrogel. In further embodiments, a method is provided for preparing a tissue-derived hydrogel. The method comprises harvesting an arterial tissue, decellularizing the tissue, and treating the arterial tissue with an elastase, thereby causing the tissue matrix to substantially swell and soften. In still further embodiments, a hydrogel prepared by any one of the methods disclosed in the present disclosure is provided. In even further embodiments, a method of treating a tissue after the removal of bulk soft tissue is provided, comprising implanting an artery-derived hydrogel into the tissue.

DESCRIPTION OF THE DRAWINGS

FIG. 4A-4F shows stained aortic tissue viewed by microscopy, as described in Example 3. FIG. 4A shows Hematoxylin (H&E) staining of fresh aorta. FIG. 4B shows H&E staining of decellularized aorta. FIG. 4C shows H&E staining of elastase-treated aorta. FIG. 4D shows Verhoff's staining of fresh aorta. FIG. 4E shows Verhoff's staining of decellularized aorta. FIG. 4F shows Verhoff's staining of elastase treated aorta.

FIG. 5A-5F shows stained aortic tissue viewed by microscopy, as described in Example 3. FIG. 5A shows Alcine blue staining of fresh aorta. FIG. 5B shows Alcine blue staining of decellularized aorta. FIG. 5C shows Alcine blue staining of elastase-treated aorta. FIG. 5D shows Trichrome staining of fresh aorta. FIG. 5E shows Trichrome staining of decellularized aorta. And FIG. 5F shows Trichrome staining of elastase-treated aorta.

FIG. 6A-6D shows Sirius Red staining of the loosely-packed collagen fiber network of a hydrogel derived from arterial tissue described in Example 3, as viewed at 4× and 10× magnifications. FIG. 6A shows the collagen network at 4× magnification under bright field. FIG. 6B shows the same view but under polarized light. FIG. 6C shows the same bright field view of the hydrogel under 10× magnification. And FIG. 6D shows the same 10× view but under polarized light.

DESCRIPTION OF ILLUSTRATIVE EMBODIMENTS

Figure 1:
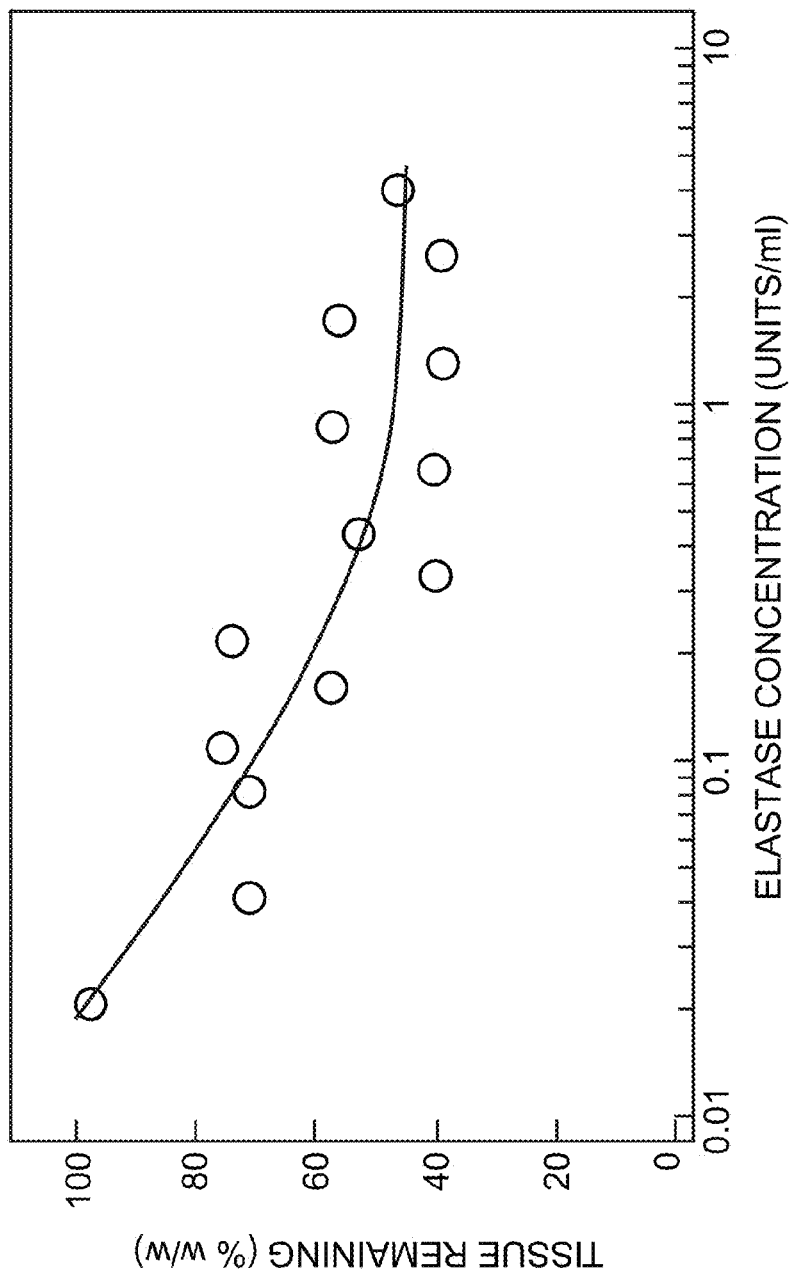
FIG. 1 is a plot of elastin degradation in porcine carotid artery as a function of elastase concentration, as described in Example 2. Elastin degradation is indicated by the loss of tissue mass as elastase degrades elastin. The percentage of tissue remaining is calculated as a percentage of weight after digestion compared to pre-digestion weight.

Reference will now be made in detail to certain exemplary embodiments according to the present disclosure, certain examples of which are illustrated in the accompanying drawings.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and all values between the endpoints.

As used herein, "hydrogel" means any soft biomaterial composed of polymer. Hydrogels may be created synthetically using artificial materials, or they may be produced by processing natural tissues. As used herein, "native" refers to the cells, tissues, or organs present in an animal prior to hydrogel implantation, or to the tissue used to form a hydrogel prior to any processing to degrade elastin or decellularize the tissue.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The present disclosure relates to hydrogels derived from acellular tissue matrices. These hydrogels can be implanted in or grafted onto a subject such as a vertebrate subject. The present disclosure also provides methods of producing tissue-derived hydrogels.

In certain embodiments, a hydrogel matrix is derived from a vertebrate arterial tissue. In some embodiments, the vertebrate arterial tissue is extracted from pig. In other embodiments, species that can serve as arterial tissue donors include, without limitation, human, non-human primates (e.g. monkeys, baboons, or chimpanzees), pig, cow, horse, goat, sheep, dog, cat, rabbit, guinea pig, gerbil, hamster, rat, or mouse. In certain embodiments, the animal that serves as an arterial tissue donor can be a transgenic animal. In further embodiments, the transgenic animal lacks expression of certain antigens, thereby increasing hydrogel tolerance after implant. In certain embodiments, the host animal tissue is altered to lack α-galactose (α-gal).

Elimination of the α-gal epitopes from the collagen-containing arterial material may diminish the immune response against the arterial material. The α-gal epitope is expressed in non-primate mammals and in New World monkeys (monkeys of South America). U. Galili et al., J. Biol. Chem. 263: 17755 (1988). This epitope is absent in Old World primates (monkeys of Asia and Africa and apes) and humans, however. Id. Anti-Gal antibodies are produced in humans and primates as a result of an immune response to the α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation of arterial material from these mammals into primates can result in rejection because of primate anti-Gal binding to the α-gal epitopes on the arterial material. The binding results in the destruction of the arterial material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-Gal antibodies.

In some embodiments, when animals that produce α-gal epitopes are used as the hydrogel tissue source, the animals are genetically engineered using methods known in the art to substantially eliminate α-gal expression. In other embodiments, α-gal is removed from harvested tissue using enzymatic processing. Removal of α-gal from host tissue can reduce the immune response that is associated with anti-Gal antibody binding to α-gal epitopes after a hydrogel is implanted in a tissue.

To enzymatically remove α-gal epitopes, after washing the tissue thoroughly with saline, the tissue sample may be subjected to one or more enzymatic treatments to remove certain immunogenic antigens, if present in the sample. In some embodiments, the tissue sample may be treated with an α-galactosidase enzyme to eliminate α-gal epitopes, if present in the tissue. In some embodiments, the tissue sample is treated with α-galactosidase at a concentration of 300 U/L prepared in 100 mM phosphate buffered saline at pH 6.0. In other embodiments, the concentration of α-galactosidase is increased to 325, 350, 375, 400, 425, 450, 475, or 500 U/L, or reduced to 275, 250, 225, or 200 U/L (or any concentration in between). In other embodiments, any suitable enzyme concentration and buffer can be used as long as sufficient antigen removal is achieved.

Alternatively, in certain embodiments animals that have been genetically modified to lack one or more antigenic epitopes may be selected as the hydrogel tissue source. For example, animals (e.g., pigs) that have been genetically engineered to lack the terminal α-galactose moiety can be selected as the tissue source. For descriptions of appropriate animals see U.S. application Ser. No. 10/896,594 and U.S. Pat. No. 6,166,288, the disclosures of which are incorporated herein by reference in their entirety. In addition, certain exemplary methods of processing tissues to reduce or remove alpha-1,3-galactose moieties are described in Xu, et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated by reference in its entirety.

In various embodiments, arterial tissue is harvested from a donor vertebrate and cleaned to remove blood. In some embodiments, the arterial tissue is first subjected to multiple rounds of freeze/thaw to disrupt the tissue. In certain embodiments, the harvested arterial tissue is then decellularized and treated with elastase to disrupt the elastin network. In some embodiments, after decellularization and elastase treatment, the arterial tissue is washed.

In various embodiments, natural hydrogel matrices derived from elastase-treated arterial tissue exhibit higher biocompatibility over artificially produced hydrogels. In certain embodiments, hydrogel matrices derived from elastase-treated arterial tissue have reduced immunogenicity compared to synthetic hydrogels when implanted in a tissue in need of treatment.

In certain embodiments, elastase-treated arterial tissue is flexible and transparent, with a consistency similar to that of silicone gel or putty. In other embodiments, elastase-treated arterial tissue swells and becomes more malleable than untreated arterial tissue. The relaxation of the extracellular matrix caused by elastin degradation allows the tissue to absorb significant amounts of water, causing the hydrogel to swell and obtain the consistency of native soft tissue. The relaxation also increases the malleability of the hydrogel, enabling it to be molded into desired forms or structures. At the same time, elastase-treated arterial tissue retains high levels of proteoglycans and other signaling molecules that can enhance biocompatibility and promote native tissue regrowth when implanted in a tissue in need of treatment. Further, elastase-treated arterial tissue retains a strong collagen network that preserves structural integrity. In further embodiments, hydrogels produced according to the methods described above retain some of their elastin network (i.e., the elastin network is only partially degraded by elastase) and thus retain a higher level of rigidity. In various embodiments, partially elastin-digested hydrogels can be used as tissue fillers where more rigid tissue fillers are required.

In certain embodiments, the malleability of elastase-treated arterial tissue provides for several beneficial properties. In further embodiments, the degraded arterial tissue can provide the physical properties normally associated with a synthetic hydrogel. Thus, the degraded arterial tissue can be molded into various shapes and used as a soft tissue implant following surgical removal of a soft tissue. In further embodiments, degraded arterial tissue retains structural integrity through the remaining collagen network. Thus, in some embodiments, rather than dissolving, dissociating, tearing, or deforming, molded arterial tissue hydrogels can retain their shape and structural integrity after implant into a soft tissue.

In various embodiments, a hydrogel matrix can be produced by decellularizing arterial tissue followed by elastase treatment. In contrast, dermis is not effective for hydrogel preparation, regardless of the elastase concentration or elastase exposure time. In further embodiments, the arterial tissue can be aortic tissue. The aorta is the largest arterial tissue region and thus can provide the most arterial tissue mass for hydrogel production. In certain embodiments, the aorta is harvested from a pig.

In various embodiments, the harvested arterial tissue is cleaned to remove blood. In some embodiments, the harvested tissue is subjected to multiple rounds of freeze/thaw to disrupt the tissue. During the freeze portion of the freeze/thaw procedure, ice crystals form, which expand and disrupt the tissue. During the thaw portion, holes or cracks are created in the tissue, which subsequently allow enzymes such as elastase to penetrate more quickly and deeply into the tissue. In some embodiments, the arterial tissue is subjected to 1, 2, 3, 4, or 5 rounds of freeze/thaw to disrupt the tissue.

In certain embodiments, harvested and cleaned arterial tissue is decellularized in a non protein-denaturing detergent solution. In further embodiments, the decellularized arterial tissue is treated with elastase to degrade elastin. In still further embodiments, after elastase treatment, the arterial tissue matrix is washed in isotonic solution.

In other embodiments, a hydrogel matrix is derived by first treating harvested arterial tissue with elastase and then decellularizing. As used herein, "harvested" arterial tissue is any portion or complete arterial tissue that has been separated from its native environment, e.g., by dissection. In certain embodiments, arterial tissue is harvested and cleaned to remove blood. In further embodiments, the harvested tissue is then treated with elastase. In still further embodiments, after elastase treatment, the tissue matrix is decellularized using a non protein-denaturing detergent solution. The decellularized tissue matrix is then washed in isotonic solution.

In further embodiments, treatment of arterial tissue with elastase and a decellularizing detergent produces a soft bulk tissue matrix. In further embodiments, the soft bulk tissue matrix has similar properties to a hydrogel. In still further embodiments, the soft bulk tissue matrix also minimizes undesirable crosslinking and retains proteoglycans and other signaling molecules that promote biocompatibility. In further embodiments, the soft bulk tissue matrix demonstrates increased biocompatibility due to the use of natural tissue materials and the high levels of glycosamino-glycans and other growth factors present in the hydrogel matrix. In further embodiments, the soft bulk tissue matrix is useful as a tissue filler for tissue regeneration after the loss of bulk soft tissue.

In various embodiments, a method is provided for preparing a tissue-derived hydrogel. In certain embodiments, the tissue to be harvested is aorta. In further embodiments, the tissue is porcine aorta. In various embodiments, the harvested tissue is first subjected to multiple rounds of freeze/thaw to break up the tissue. The harvested tissue is then rinsed with saline. In some embodiments, the saline is a 0.9% saline solution. In other embodiments, the saline concentration is reduced to 0.5%, 0.6%, 0.7%, or 0.8%, or is increased to 1.0%, 1.1%, 1.2%, 1.3%, 1.4%, or 1.5% saline solution. The harvested tissue is then washed in a buffer solution. In certain embodiments, the buffer solution is Tris-HCL. In further embodiments, the Tris-HCL is at a concentration of between 30 mM and 120 mM (i.e., at 30 mM, 40 mM, 50 mM, 60 mM, 70 mM, 80 mM, 90 mM, 100 mM, 110 mM, or 120 mM, or any concentration in between). In still further embodiments, the buffer solution also contains at least one antibiotic. In even further embodiments, the buffer contains 1.5 µg/ml of amphotericin, 65 µg/ml of streptomycin and 65 units/ml of penicillin. In other embodiments, the concentration of amphotericin is decreased to 1.0, 1.1, 1.2, 1.3, or 1.4 µg/ml, or increased to 1.6, 1.7, 1.8, 1.9, or 2.0 µg/ml (or any concentration in between). In certain embodiments, the concentration of streptomycin is decreased to 60, 61, 62, 63, or 64 µg/ml, or increased to 66, 67, 68, 69, or 70 µg/ml (or any concentration in between). In some embodiments, the concentration of penicillin is decreased to 60, 61, 62, 63, or 64 µg/ml, or increased to 66, 67, 68, 69, or 70 µg/ml (or any concentration in between). In further embodiments, the harvested tissue is washed in Tris-HCL for 10 minutes. In other embodiments, the harvested tissue is washed in Tris-HCL for 5, 6, 7, 8, 9, 10, 11, 12, 13, 14, 15, 20, 25, 30, 45, or 60 minutes (or any time in between).

In various embodiments, the harvested tissue is then treated with elastase. In certain embodiments, between 0.021 and 5.35 units/ml of elastase are added to the Tris buffer to digest elastin. See FIG. 1. Increasing the elastase concentration does not necessarily result in a faster or more complete elastin degradation. An elastase enzyme unit is defined as the amount of enzyme that will hydrolyze 1.0 pmole of N-succinyl-L-Ala-Ala-Ala-p-nitroanilide per min at pH 8.0 and at 25° C. In further embodiments, between 0.1 and 5 units/ml of elastase are added. In still further embodiments, 0.3 units/ml of elastase is added. In even further embodiments, 0.5 units/ml of elastase is added. In further embodiments, 1 unit/ml of elastase is added. In yet another embodiment, 2 units/ml of elastase is added. In still further embodiments, 0.025, 0.05, 0.075, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3 or 5.35 units/ml of elastase, or any concentration in between, are added.

The tissue to be digested is incubated with elastase for between 10 and 96 hours, depending on the concentration of elastase and the desired percentage of total elastin degradation. In certain embodiments, the elastase incubation time or is increased in order to more fully degrade elastin in the tissue. In other embodiments, the elastase incubation time is reduced in order to preserve more elastin in the tissue following digestion. In some embodiments, the tissue to be digested is incubated with elastase for 10, 11, 12, 13, 14, 15, 16, 17, 18, 19, 20, 24, 30, 36, 48, 60, 72, 84, or 96 hours (or any time in between). In one embodiment, porcine aorta tissue is incubated with elastase for 18 hours. In certain embodiments, the tissue is agitated during elastase treatment. Such agitation may be gentle or more intense. In further embodiments, the agitation involves shaking the tissue. In some embodiments, elastase-digested tissue is then washed in saline solution. In certain embodiments, washing is conducted for 30 minutes. In other embodiments, washing is conducted for 10, 20, 30, 40, 50, 60, 90, or 120 minutes.

In various embodiments, the elastase-digested tissue is then decellularized using a non protein-denaturing detergent solution. In certain embodiments, the detergent that is selected does not disrupt the structural integrity or alter the functional properties of the tissue matrix during decellularization. In some embodiments, the detergent is sodium deoxycholate (SDC). In other embodiments, the detergent is sodium dodecyl sulfate (SDS), Triton-X 100 or a combination of SDC, SDS, and/or Triton-X 100. In other embodiments, any known decellularization detergent can be used. In certain embodiments, the concentration of detergent is calibrated using techniques known to one of skill in the art to ensure that the tissue is completely decellularized. In even further embodiments, 2% sodium deoxycholate is used.

In some embodiments, the detergent solution is applied for at least 24 hours (e.g., at least 24, 25, 26, 27, 28, 29, 30, 36, 48, 60, or 72 hours, or any time in between). In certain embodiments, the detergent solution is applied for at least 60 hours (e.g., at least 60, 65, 70, 75, 80, 85, 90, or 120 hours, or any time in between). In further embodiments, a 2% sodium deoxycholate solution is applied for 64 hours at 4 degrees Celsius to decellularize harvested porcine aortic tissue. In various embodiments, the decellularized tissue is then washed to remove detergent and lysed cells. In certain embodiments, the wash solution is saline or any saline-containing solution. In other embodiments, the wash solution is phosphate buffered saline (PBS) and ethylenediaminetetraacetic acid (EDTA). In some embodiments, the wash solution is PBS at pH 7.4 and 5 mM EDTA. In further embodiments, the decellularized tissue is washed for at least one hour (e.g., at least 1, 2, 3, 4, 5, 6, 7, 8, 9, 10, 11, 12, 18, 24, 36, or 48 hours, or any time in between). In even further embodiments, decellularized tissue is washed for at least 10 hours. In even further embodiments, the washing is done at nearly room temperature or at any temperature between and including room temperature and 4 degrees Celsius (e.g., at a temperature of 30, 29, 28, 27, 26, 25, 24, 23, 22, 21, 20, 18, 15, 10, 5, 4, 3, 2, or 1 degree Celsius, or any temperature in between).

In various embodiments, hydrogels produced by the above methods can subsequently be cryopreserved. In certain embodiments, the hydrogel is incubated in a cryopreservation solution. In further embodiments, the cryopreservation solution includes one or more cryoprotectants to minimize ice crystal damage to the hydrogel's structural matrix. In certain embodiments, the hydrogel can be cryopreserved by placing it in the cryopreservation solution and then freezing it in a freezer at approximately −80 degrees Celsius (e.g., at −75, −80, or −85 degrees Celsius, or any temperature in between), or by plunging the hydrogel into liquid nitrogen and storing frozen until use.

In various embodiments, hydrogels are cryopreserved for storage by freeze-drying. In certain embodiments, the hydrogel is placed in a cryopreservation solution that includes components, such as an organic solvent or water, to protect against damage during freeze drying. In further embodiments, following incubation in the cryopreservation solution, the hydrogel is placed in a sterile vessel that is permeable to water vapor but impermeable to bacteria. The vessel is cooled to a low temperature at a specified rate that is compatible with the specific cryoprotectant formulation to minimize the freezing damage. The hydrogel is then dried at a low temperature under vacuum conditions. At the completion of the drying, the vacuum of the freeze drying apparatus is reversed with a dry inert gas such as nitrogen, helium or argon. The hydrogel is then sealed in an impervious container and stored until use. While the example above describes one method for cryopreservation, one of skill will recognize that other such methods known in the art may be used to cryopreserve and store hydrogels.

In certain embodiments, artery-derived hydrogels produced according to the methods described above retain some of the structural and functional aspects found in untreated tissue. In various embodiments, the biological functions retained include the ability to support native tissue spreading, native cell proliferation, and native cell differentiation. In certain embodiments, the hydrogel retains growth factors (such as type I collagen, glycosaminoglycans, or proteoglycans) that serve to promote tissue and cell regeneration or growth. In various other embodiments, the retained physical properties of hydrogels (such as the maintenance of the three dimensional collagen network and its strength, ductility and elasticity) enhance cell growth and tissue spreading. In certain embodiments, the efficiency of the biological function of a tissue-derived hydrogel can be measured by the ability of the hydrogel to support cell proliferation. In further embodiments, the hydrogel is able to promote at least 75%, 50%, 30%, 25%, or 10% (or any percentage in between) of the proliferation that would occur on a native tissue or organ scaffold.

While a hydrogel to be implanted in a vertebrate can be produced from the same species and the same organ as the host, this is not a requirement. In various embodiments, the hydrogel should retain biocompatibility and amenability to cell proliferation and tissue growth when implanted in a host tissue. Thus, in certain embodiments, a hydrogel derived from the tissue of one species can be implanted in another species. Exemplary species that can serve as hydrogel tissue donors include, without limitation, human, non-human primates (e.g. monkeys, baboons, or chimpanzees), pig, cow, horse, goat, sheep, dog, cat, rabbit, guinea pig, gerbil, hamster, rat, or mouse. Likewise, in certain embodiments, a hydrogel derived from one tissue source can be implanted into a different host tissue. In further embodiments, hydrogels derived from porcine artery (such as aorta) are implanted in various human tissues.

In various embodiments, artery-derived hydrogels can be provided in variety of forms and sizes depending on the tissue or organ into which it will be implanted. Thus, in certain embodiments, the hydrogel can be provide in strips or sheets. In other embodiments, the hydrogel is provided in unmolded balls or cylinders that can later be manipulated to assume various structures. In even further embodiments, hydrogels are provided pre-formed to achieve a desired structure for a given tissue implant use. In other embodiments, an artery-derived hydrogel is provided as a moldable putty that will conform to the shape of the space in which it is implanted. For example, the moldable hydrogel can conform, after implantation, to the shape of a void space in a recipient tissue caused by surgical removal of tissue (e.g., tumor removal).

In some embodiments, the artery-derived hydrogel comprises a loose collagen network that is rich in glycosaminoglycans and other growth factors. In further embodiments, the elastin in an artery-derived hydrogel tissue is partially or completely degraded. See FIG. 2.

Unlike dermal or other tissues, arterial tissue contains a high density of elastin. In some instances, 40 to 50% of the arterial tissue is composed of elastin, allowing the native artery to swell and contract with blood flow. Thus, in some embodiments, elastin degradation disrupts a significant component of the arterial tissue and causes significant swelling and tissue softening that is not observed when other tissues are degraded with elastase, preventing their use as hydrogels. In further embodiments, swelling is due to increased tissue matrix hydration. In certain embodiments, elastase-treated tissue matrices swell by 200 to 300% as compared to undigested arterial tissue when placed in aqueous solution (e.g., elastase-treated tissue matrices swell by 200, 225, 250, 275, or 300%, or any percentage in between). In further embodiments, hydrogels produced from porcine aortic tissue swell by an average of 278% after elastase treatment, decellularization and placement in an aqueous solution. In further embodiments, the swelling of arterial tissue induced by elastase treatment produces a soft, putty-like foam.

In certain embodiments, artery-derived hydrogels are molded into various shapes and demonstrate a good ability to retain that structure over time. In further embodiments, the artery-derived hydrogels retain structural integrity (i.e., the hydrogel remains in one piece) after mechanical manipulation. In even further embodiments, aorta-derived hydrogels retain structural integrity after application of tensile or torsional forces.

In various embodiments, artery-derived hydrogels can be used as tissue fillers for tissue repair or treatment. In certain embodiments, artery-derived hydrogels are used as implants for the face or neck. In further embodiments, artery-derived hydrogels are used as tissue fillers for tissue regeneration after the loss of bulk soft tissue. In certain embodiments, artery-derived hydrogels are implanted into a tissue after the loss of bulk soft tissue and swell to fill the region of lost tissue. In even further embodiments, artery-derived hydrogels are used as tissue fillers after lumpectomies. In still further embodiments, artery-derived hydrogels are implanted after a lumpectomy and serve to coagulate blood from the operation site, reducing the need for a drain.

It has been shown that after tumor removal, tissue regrowth is poor, especially as to the subcutaneous tissue layers. Generally, a layer of skin will regrow after tumor removal, but the underlying tissue remains unregenerated. Thus, in various embodiments, artery-derived hydrogels can be used as implants for the face or neck after tumor removal. In certain embodiments, such implants serve as tissue fillers that can provide the face or neck with a more natural look after tumor removal. In further embodiments, such implants serve as scaffolds for tissue regeneration and/or repair by providing a structural matrix for native cell migration and/or proliferation. In still further embodiments, such implants help coagulate blood at the site of tumor removal and reduce the need for a drain. In even further embodiments, such implants promote tissue repair or regeneration due to the high levels of glycosamino-glycans and other growth factors retained in the hydrogel.

In various embodiments, artery-derived hydrogels can be used as delivery vehicles for pharmaceutical agents. In certain embodiments, artery-derived hydrogels are impregnated with a pharmaceutical agent using techniques known to one of skill in the art. In further embodiments, impregnated hydrogels are then implanted in a tissue in need of the pharmaceutical agent. In even further embodiments, implanted hydrogels containing pharmaceutical agents can serve as time-release carriers for a pharmaceutical agent, releasing the pharmaceutical agent as the implanted hydrogel is gradually dissolved and reabsorbed into the tissue. In various embodiments, the pharmaceutical agent is an anticancer agent such as paclitaxel, 5-fluorouracil, bleomycin A2 and mitomycin C, methotrexate, or doxorubicin. In further embodiments, the pharmaceutical agent is a growth factor such as fibroblast growth factor, transforming growth factor, bone morphogenetic protein, vascular endothelial growth factor, nerve growth factor, or insulin-like growth factor. In still further embodiments, the pharmaceutical agent is a pain relief agent such as oxycodone HCl, morphine sulfate, or tramadol. And in yet further embodiments, the pharmaceutical agent is an antimicrobial agent such as chlorhexidine, ciprofloxacin, clarithromycin, chloramphenicol, ceftriaxone, ofloxacin, polymycin B, sulfamethoxazole, streptomycin, tobramycin, tetracycline, or trimethoprim. In some embodiments, the hydrogel is impregnated with combinations of at least two pharmaceutical agents (e.g. at least 2, 3, 4, 5, 6, 7, 8, 9, or 10 agents). In certain embodiments, the hydrogel containing the pharmaceutical agent is implanted into a tissue after the removal of bulk soft tissue. In further embodiments, the hydrogel containing the pharmaceutical agent is implanted in a tissue in need of cancer treatment or therapy. In some embodiments, the hydrogel containing the pharmaceutical agent is implanted in a chronic wound site.

The following examples serve to illustrate, and in no way limit, the present disclosure.

EXAMPLES

Example 1

Decellularization of Porcine Arteries and Aorta

Porcine carotid arteries (about 10 to 20 cm long) or aorta were harvested by manual dissection. Blood clots in arteries and aorta were washed off before decellularization. Carotid arteries and aorta were decellularized at room temperature (22 to 25° C.) for 24 hours in a 10 mM HEPES buffer solution (pH 8.0) containing 1% (w/v) Triton X-100 and 10 mM EDTA with gentle agitation on a shaker. Decellularized arteries and aorta were washed with 0.9% saline to remove the detergent (i.e., Triton x-100) until foam was no longer observed. Arteries and aorta were then treated at room temperature (22 to 25° C.) for 24 hours in second HEPES buffer solution (10 mM, pH 7.4) containing 30 units/ml DNase, 50 µg/ml gentamicin, 2 mM calcium chloride and 2 mM magnesium chloride. The DNase solution was discarded, and tissue was washed three times with 0.9% saline (10 min each time). Histological evaluation (H&E stain) and biochemical tests demonstrated that the process completely decellularized harvested porcine arteries and aorta. In some cases, decellularized arteries and aorta were further treated in phosphate-buffered saline (pH 6.5) containing 0.2 unit/ml α-galactosidase and 50 mM ETDA. This step eliminated extracellular α-gal epitopes of porcine tissue.

Example 2

Removal of Elastin from Porcine Carotid Arteries

This experiment was intended to identify the effective range of elastase concentration and time course of elastin removal from porcine carotid arteries and aorta. Fresh porcine carotid arteries were harvested by manual dissection. Arteries were washed in saline to clean blood clots, and cut into small pieces (1 mm×1 mm). Samples of 80 mg tissue in microtubes were treated in 0.5 ml Tris-HCl buffer (100 mM, pH 8.0) containing elastase of between 0.011 and 5.35 units per ml for 22 hours. After incubation, samples were centrifuged, pellets of samples were washed with de-ionized water, and centrifuged again. Sample pellets were then lyophilized, and the percentage of tissue remaining after elastase treatment was calculated. FIG. 1 demonstrated that elastase at concentration from 0.021 unit/ml to 5.35 units per ml was effective in digesting elastin in porcine arteries. On average, porcine carotid arteries contained about 50% (w/w) elastin. When 5.35 units/ml elastase was used, the elastin content of porcine carotid artery was reduced by 79±14% after 22 hour digestion.

Figure 2:
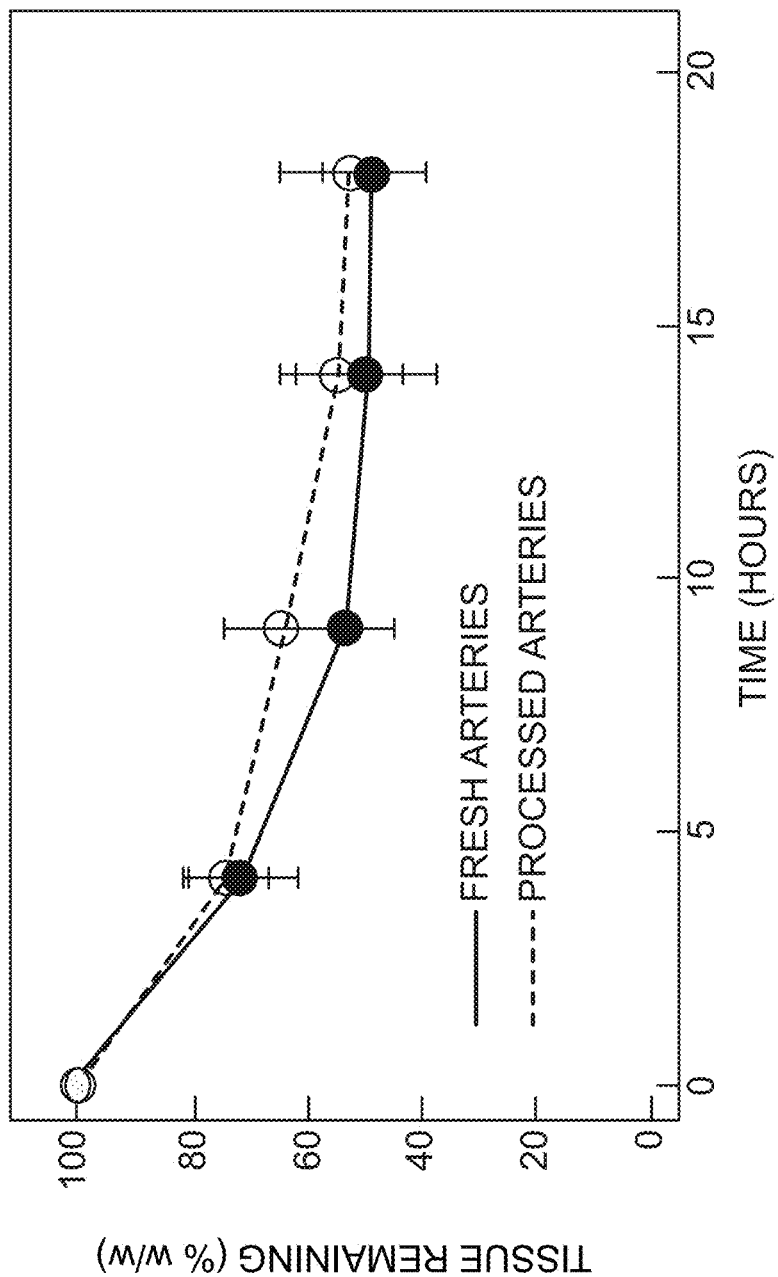
FIG. 2 is a plot of elastin degradation plotted as a function of time, as described in Example 2. The dotted curve represents elastin degradation in tissue that has been decellularized prior to elastin degradation. The solid curve represents elastin degradation in tissue that has not yet been decellularized when treated with elastase. Elastin degradation is indicated by the loss of tissue mass over time. The percentage of tissue remaining is calculated as a percentage of weight after digestion compared to pre-digestion weight.

A comparison was made between freshly harvested carotid arteries and decellularized arteries. Both fresh and decellularized arteries were cut into small pieces (1 mm×1 mm). 80 mg tissue samples in microtubes were treated in 0.5 ml Tris-HCl buffer (100 mM, pH 8.0) containing 0.67 unit/ml elastase for 5, 8, 14, and 18 hours. At the end of each incubation point, samples were centrifuged, pellets of samples were washed with de-ionized water, centrifuged again. Sample pellets were lyophilized, and the percentage of tissue remaining after elastase treatment was calculated. As shown in FIG. 2, fresh arteries and decellularized arteries had comparable reaction curves. At 0.67 unit/ml elastase, the reaction was complete after 18 hours.

Example 3

Removal of Elastin from Porcine Aorta

Figure 3:
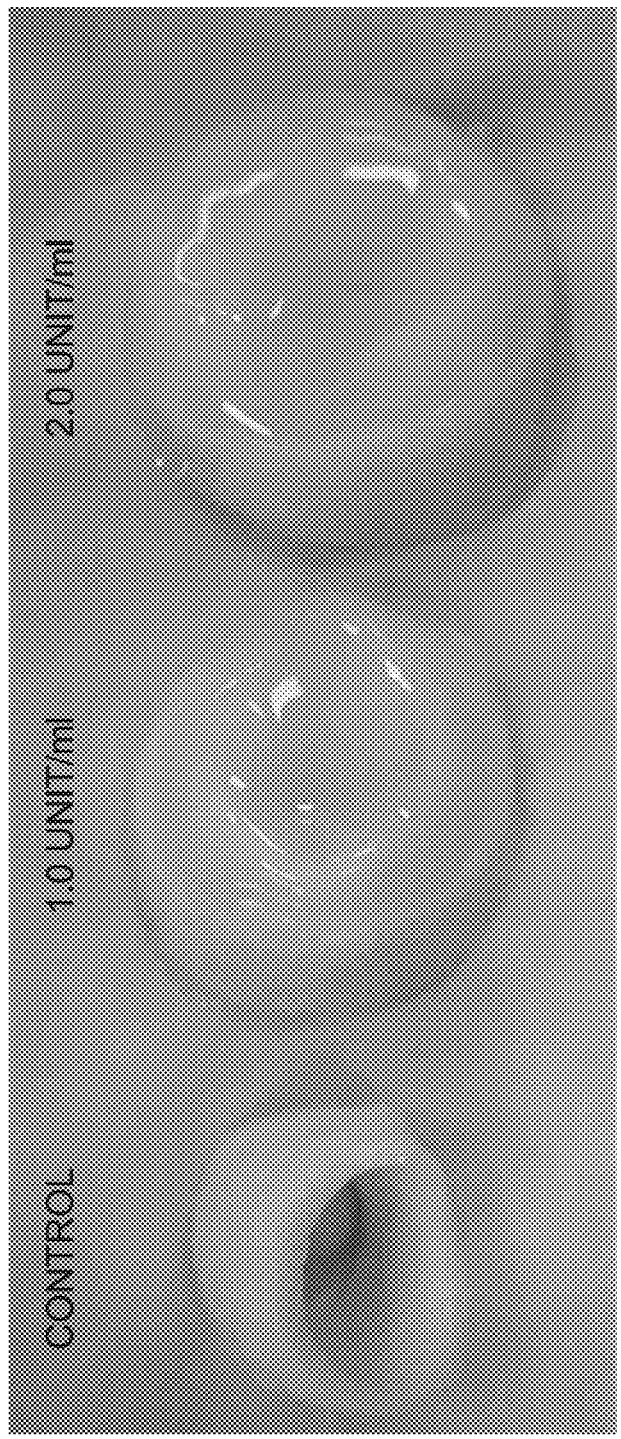
FIG. 3 shows examples of porcine aorta treated with elastase, as described in Example 3. At the left is a sample of untreated aorta. The middle sample is aorta that has been treated with 1.0 units/ml of elastase, as described in Example 3. At the right is a sample of aorta treated with 2.0 units/ml of elastase, as described in Example 3.

Decellularized aorta (produced as described in Example 1) was washed with 100 mM Tris-HCl buffer (pH 8.0) for 10 minutes. 2-gram tissue samples (wet weight) were treated at room temperature for 18 hours in 20 ml of 100 mM Tris-HCl buffer (pH 8.0) containing 1.0 unit/ml or 2 unit/ml elastase. Tissue material was washed in 0.9% saline for 30 min. FIG. 3 shows the gross appearance of elastase-treated aorta sections. After elastase treatment and washing, the aorta tissue became a structured, soft hydrogel.

In a second experiment, histological evaluation was used to compare fresh, decellularized, and elastase-treated aorta tissues. Decellularization of aorta tissue was done at room temperature for 5 hours in a 10 mM HEPES buffer solution (pH 8.0) containing 1% (w/v) Triton x-100 and 10 mM EDTA. Elastase treatment was done for 49 hours in 100 mM Tris-HCl buffer (pH 8.0) containing 0.5 unit/ml elastase. The tissue to solution ratio was 10 ml solution per 1 gram wet aorta tissue. Decellularized and elastase-treated tissue samples were washed in 10 mM HEPES buffer solution. Samples were processed, and stained for histological evaluation (H&E, Verhoffs, Alcine blue and Trichrome stains). FIG. 4 and FIG. 5 show the characteristic histological structures of fresh aorta tissues, and the retention of the tissue's structural integrity after decellularization. However, elastase treatment resulted in tissue swelling and substantial change in the tissue structures (i.e., loosening).

Figure 7:
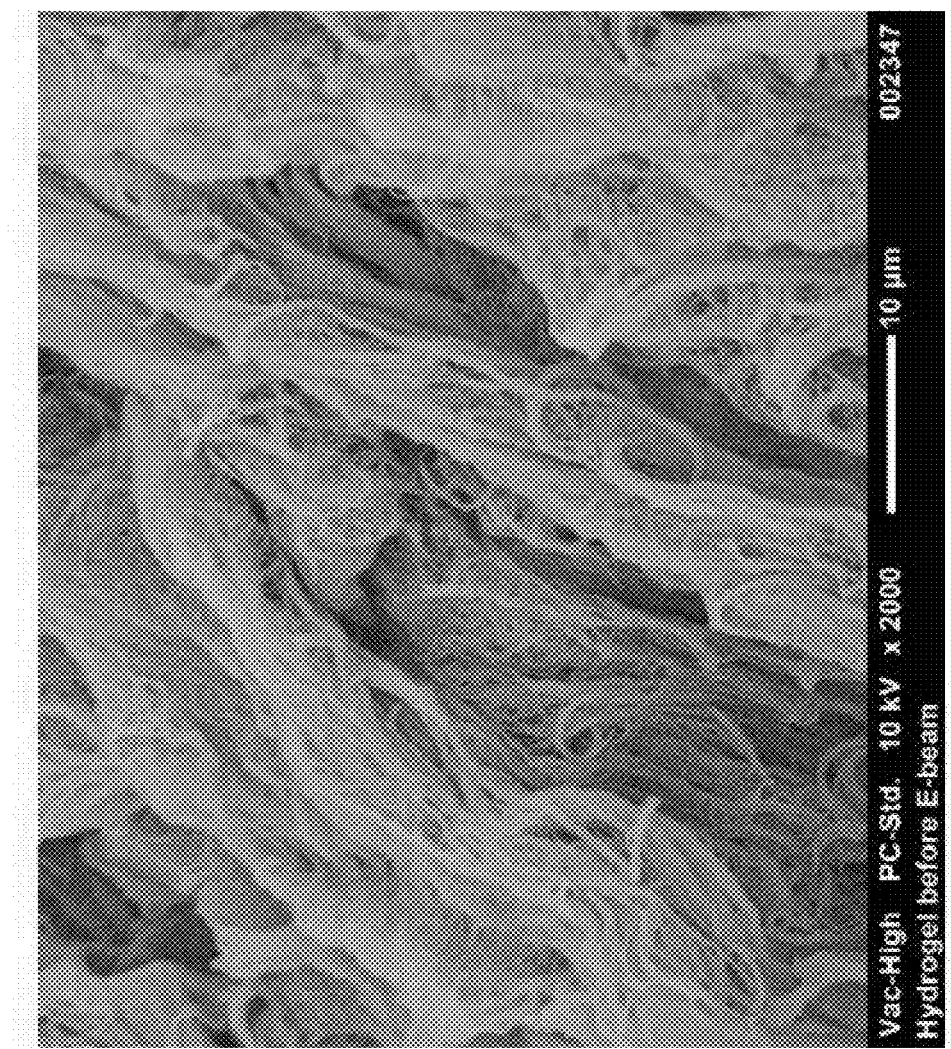
FIG. 7 is a scanning electron micrograph image of an artery-derived hydrogel, as described in Example 3.
Figure 8:
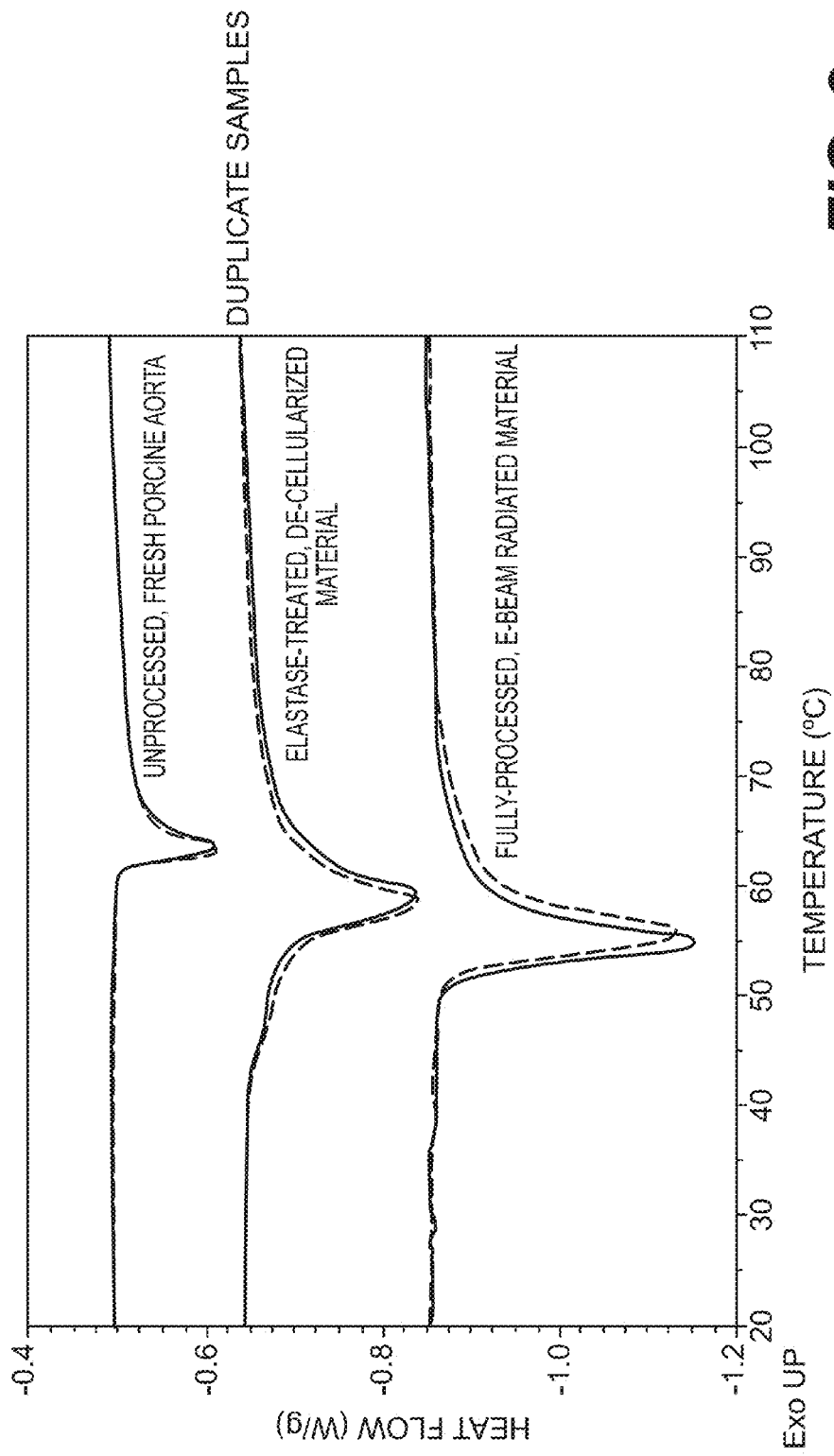
FIG. 8 is a graph showing examples of differential scanning calorimetry (DSC) thermograms for fresh porcine aorta and hydrogels, produced as described in Example 3, before and after e-beam sterilization (17.5 kGy).

In a third experiment, harvested fresh porcine aorta was rinsed with 0.9% saline, and cut open for elastase treatment. Aortic tissue (14 grams) was treated at room temperature for 72 hours in 150 ml Tris-HCl buffer (50 mM, pH 8.0) containing 0.3 unit/ml elastase, 65 units/ml penicillin, 1.5 µg/ml amphotericin and 65 µg/ml streptomycin. After elastase treatment, tissue material was washed for 2 hours in a 2% (w/v) sodium deoxycholate detergent solution. The solution of 2% sodium deoxycholate was then refreshed, and aorta tissue material was washed at 4° C. for an additional 62 hours. In order to remove sodium deoxycholate, aorta tissue material was washed three times (10 hours each) in phosphate-buffered saline (pH 7.4) containing 5 mM EDTA. After processing, the tissue was weighed to be 53 grams, and had increased in volume by 278% as compared to the pre-treatment volume. FIG. 6 shows the network of loosely-packed collagen fibers in an aorta-derived hydrogel. The translucent, thin slices (~2 mm thick) of aorta-derived hydrogel shown in FIG. 6 were stained with picosirius red, and photos were taken under bright field and polarized light. A loosely-packed collagen fiber network that supports biochemical components and structural elements is visible in FIG. 6. FIG. 7 shows the fine ultrastructure of an aorta-derived hydrogel material. Differential scanning calorimetry was also used to evaluate the change in stability of aorta tissue after hydrogel processing (FIG. 8). The elastase treatment alters the thermogram data plots significantly. The onset denaturation temperature has decreased and denaturation enthalpy increased. Decellularization alone does not change these two parameters. The decrease of the onset denaturation temperature is related to the enhanced hydration of the tissue after elastase treatment, and the enthalpy change could be attributed to the loss of elastin. However, with a denaturation temperature of less than 50° C. after e-beam sterilization, the hydrogel material is sufficiently stable at body temperature.

Example 4

Biomechanical Properties of Aorta-Derived Hydrogels

Figure 9:
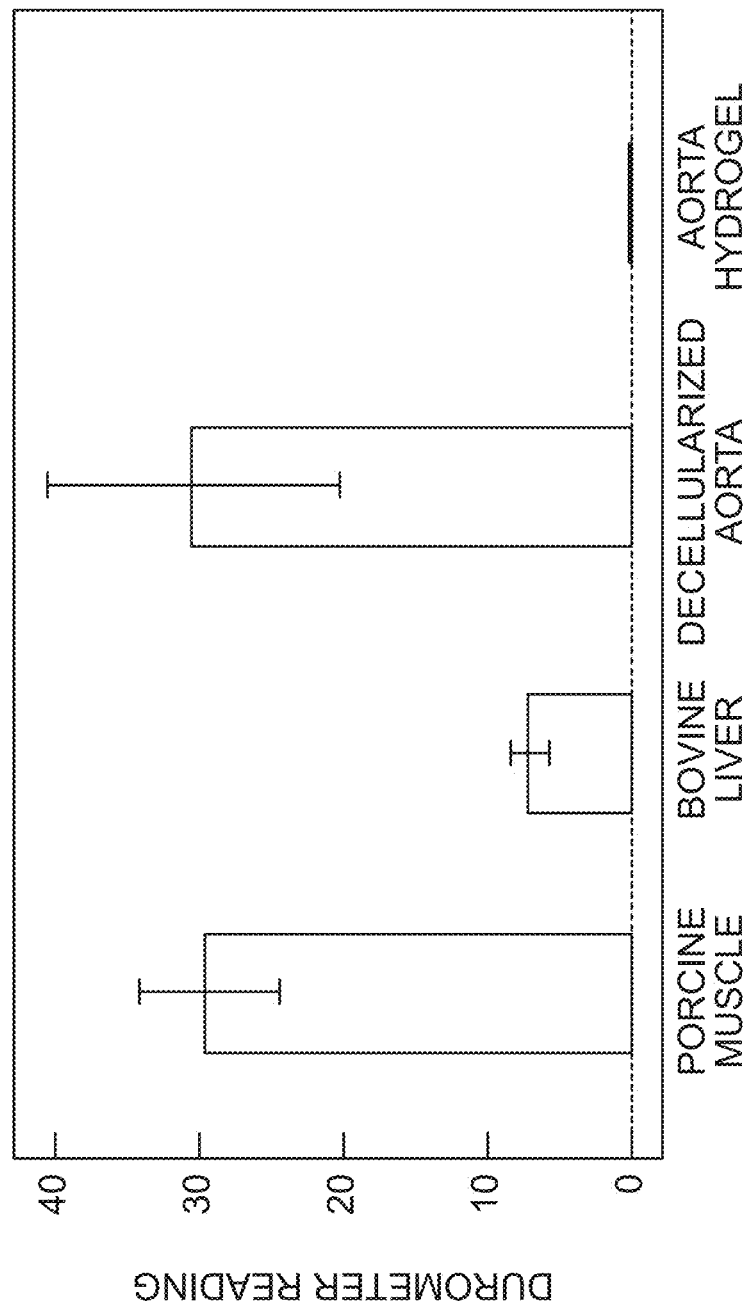
FIG. 9 is a graph showing the softness and flexibility of porcine muscle, bovine liver, decellularized aorta, and aorta-derived hydrogel as measured by a durometer.
Figure 10:
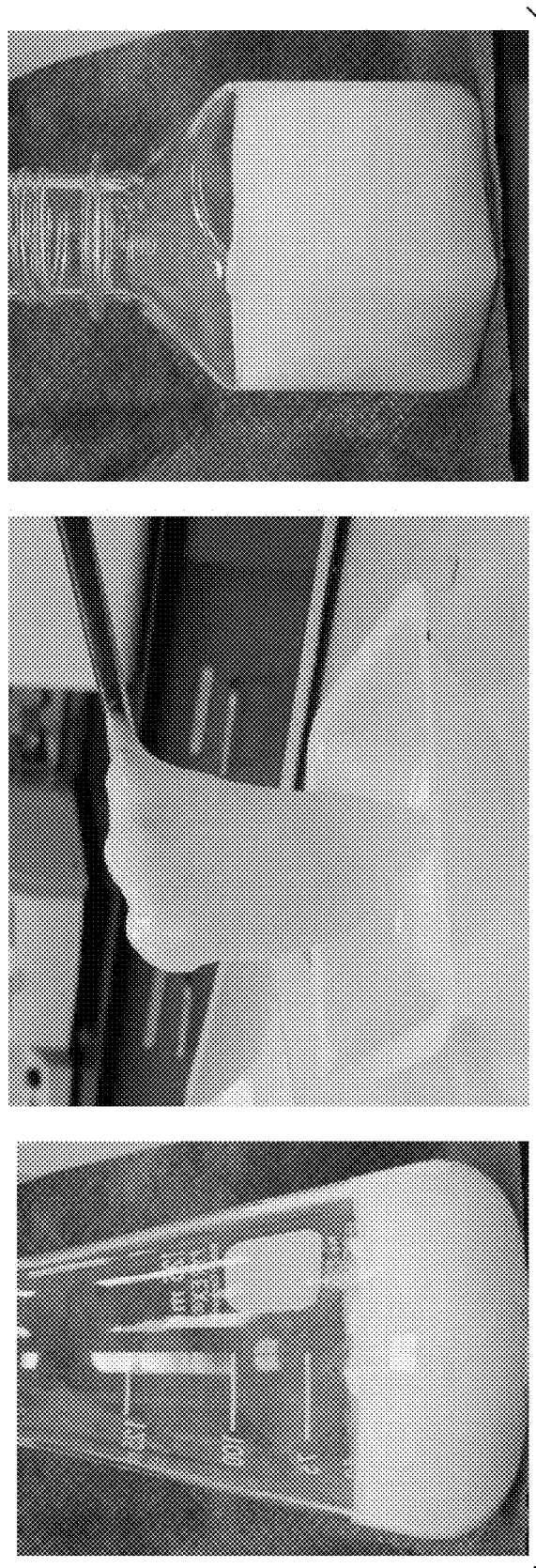
FIG. 10 shows that aorta-derived hydrogels conform to the shapes of the containers in which they are placed.

The softness and flexibility of aorta-derived hydrogels (N=4) was analyzed by a durometer. A durometer measures the indentation resistance of elastomeric or soft materials based on the depth of penetration of a conical indentor. Hardness values range from 0 to 100. A lower durometer reading indicates a softer material, whereas a higher number indicates that the material is harder. Durometer measurements were taken in five spots for each hydrogel sample tested. Porcine muscle, bovine liver and decellularized aorta were tested at the same time for comparison. Mean durometer values for porcine muscle, bovine liver and decellularized aorta were 29.4±4.9, 7.2±1.4, and 30.5±10.0, respectively (mean±SD; N=4). Durometer readings were zero for all aorta-derived hydrogel samples (FIG. 9). Aorta-derived hydrogels are soft and flexible enough that when multiple pieces were placed together in a container, they conformed to the shape of the container, produce a flat surface, and left no empty space between the pieces (FIG. 10).

While the above examples involved the production, structure, and use of porcine aorta and carotid artery in hydrogels, one of skill would recognize that other tissues could be used to produce tissue-derived hydrogels having desired properties.

Other embodiments of the disclosed devices and methods will be apparent to those skilled in the art from consideration of the specification and practice of the devices and methods disclosed herein.

What is claimed is:

1. A method of treating a tissue after the removal of bulk soft tissue, comprising implanting an aorta-derived hydrogel into the tissue, wherein the hydrogel comprises a decellularized aorta tissue from which some but not all of the elastin has been removed by exposing the tissue to elastase at a concentration of between about 0.021 and 5.35 units/ml for 5 to 96 hours, and wherein the aorta tissue used to prepare the hydrogel has been subjected to at least one round of freezing and thawing followed by decellularization and removal of at least some elastin from the tissue, and wherein the tissue is not cross-linked prior to implantation.

2. The method of claim 1, wherein the hydrogel swells to fill the region of bulk soft tissue that has been removed.

3. The method of claim 1, wherein the hydrogel promotes tissue repair and regeneration.

4. The method of claim 1, wherein the tissue removal is a lumpectomy.

5. The method of claim 1, wherein the hydrogel is impregnated with a pharmaceutical agent and releases the pharmaceutical agent over time as the implanted hydrogel is gradually dissolved and reabsorbed into the tissue.

6. The method of claim 5, wherein the pharmaceutical agent is an anticancer agent, a growth factor, a pain relief agent, an antimicrobial agent, or combinations thereof.

* * * * *